United States Patent
Cheng et al.

(10) Patent No.: US 9,314,733 B2
(45) Date of Patent: Apr. 19, 2016

(54) METHOD FOR DETECTING LOSS OF DESULFURIZATION ORGANIC COMPONENTS AND REGENERABLE FLUE GAS DESULFURIZATION PROCESS

(71) Applicants: Yong Cheng, Panzhihua (CN); Jianming Li, Panzhihua (CN)

(72) Inventors: Yong Cheng, Panzhihua (CN); Jianming Li, Panzhihua (CN)

(73) Assignee: PANGANG GROUP PANZHIHUA IRON & STEEL RESEARCH INSTITUTE CO., LTD (CN)

( * ) Notice: Subject to any disclaimer, the term of this patent is extended or adjusted under 35 U.S.C. 154(b) by 15 days.

(21) Appl. No.: 14/262,287

(22) Filed: Apr. 25, 2014

(65) Prior Publication Data

US 2014/0322117 A1 Oct. 30, 2014

(30) Foreign Application Priority Data

Apr. 27, 2013 (CN) .......................... 2013 1 0151286

(51) Int. Cl.
| | | |
|---|---|---|
| *B01D 53/50* | (2006.01) | |
| *B01D 53/48* | (2006.01) | |
| *B01D 53/00* | (2006.01) | |
| *B01D 53/14* | (2006.01) | |
| *G01N 1/28* | (2006.01) | |

(52) U.S. Cl.
CPC ........ *B01D 53/1425* (2013.01); *B01D 53/1481* (2013.01); *B01D 53/1493* (2013.01); *B01D 53/50* (2013.01); *B01D 2252/204* (2013.01); *B01D 2258/025* (2013.01); *B01D 2258/0283* (2013.01); *G01N 2001/2893* (2013.01); *Y10T 436/17* (2015.01); *Y10T 436/173845* (2015.01)

(58) Field of Classification Search
CPC ........ B01D 53/50; B01D 53/48; B01D 53/46; B01D 53/34; B01D 53/00; Y10T 436/173845; Y10T 436/17; Y10T 436/00

USPC .............. 436/119, 111, 106; 423/242.1, 210; 422/242.1, 210

See application file for complete search history.

(56) References Cited

U.S. PATENT DOCUMENTS

| 2006/0024839 A1* | 2/2006 | Petropavlovskikh et al. 436/178 |
| 2009/0000990 A1* | 1/2009 | Toida ............................ 208/219 |

FOREIGN PATENT DOCUMENTS

| CN | 1688879 A | 10/2005 |
| CN | 102539563 | * 7/2012 ............. C01N 30/02 |

OTHER PUBLICATIONS

CN 102539563 Machine Translation in English. Obtained on Jul. 2, 2015. pp. 1-24.*
STN Search Report obtained on Jun. 30, 2015. pp. 1-119.*

* cited by examiner

*Primary Examiner* — Christine T Mui
(74) *Attorney, Agent, or Firm* — Blank Rome LLP

(57) ABSTRACT

A method for detecting paths and amount of loss of desulfurization organic components in a flue gas desulfurization system includes preparing a to-be-measured solution and a base standard solution, and diluting the base standard solution with water to a plurality of standard solutions containing different concentrations of desulfurization organic components; adjusting the to-be-measured solution and standard solutions to have a strong acidity, respectively, such that each of desulfurization organic components in the to-be-measured solution and standard solutions exists in ion forms; heating and oscillating the to-be-measured solution and standard solutions, respectively; respectively detecting carbon elements in the standard solutions, to form a linear relationship between concentrations of the desulfurization organic components in the standard solutions and detected carbon element data; and detecting carbon elements in the to-be-measured solution, and obtaining a total concentration of the desulfurization organic components in the to-be-measured solution according to the linear relationship.

8 Claims, 1 Drawing Sheet

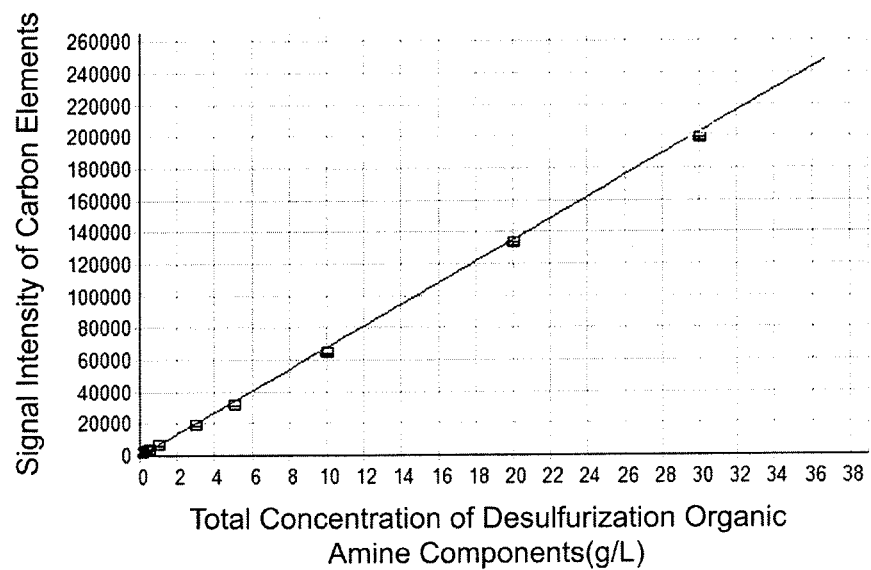

METHOD FOR DETECTING LOSS OF DESULFURIZATION ORGANIC COMPONENTS AND REGENERABLE FLUE GAS DESULFURIZATION PROCESS

FIELD OF THE INVENTION

The present disclosure relates to a technical filed of detection and analysis, and more particularly, to a method for detecting paths and amount of loss of desulfurization organic components in a flue gas desulfurization system, and a regenerable flue gas desulfurization process capable of monitoring loss of desulfurization organic components in a flue gas desulfurization process in real time by using the method.

DESCRIPTION OF RELATED ART

In a flue gas desulfurization (FSD) process of the prior art, a desulfurizing solution such as an organic amine desulfurizing solution or the like is typically used to absorb sulfur oxides, e.g., sulfur dioxide and sulfur trioxide, in a flue gas at a lower temperature, and then desorb the sulfur oxides absorbed in the desulfurizing solution at a higher temperature, so that sulfur oxide gases having a higher purity can be obtained, while obtaining a desulfurizing solution having a capability of absorbing sulfur oxides recovered. That is to say, the desulfurizing solution used in the flue gas desulfurization process can be recycled, and as a result, the flue gas desulfurization process can recycle. Accordingly, the process is also generally referred to as a regenerable flue gas desulfurization process. Typically, a flue gas desulfurization system contains apparatuses and materials used for the flue gas desulfurization process described as above. The flue gas desulfurization process is widely used to treat flue gases discharged in industrial production including metallurgy, sintering, power plant boilers, or the like, which is important for reducing environmental pollution caused by sulfur oxides in the flue gases, and which can also recover and reuse the sulfur oxides contained in the flue gas for producing industrial raw materials such as sulfuric acid, sulphur or the like. In addition, the regenerable flue gas desulfurization process eliminates process disadvantages existing in traditional flue gas desulfurization processes such as a limestone-gypsum wet process, avoiding side effects of generating new solid waste pollutants or increased emission of carbon dioxide as greenhouse gas or the like.

Generally, a desulfurization solution contains organic components (referred to as organic desulfurization components herein) capable of absorbing sulfur oxides including sulfur dioxide and sulfur trioxide in a flue gas at a lower temperature and desorbing the sulfur oxides at a higher temperature, which are the core components of the desulfurization solution.

For example, an organic amine desulfurization solution is prepared by dissolving one or more organic amine-based compounds at a concentration ratio in water and then adding a small amount of an active agent, an antioxidant and/or the like thereto. Such an organic amine desulfurization solution has good absorption and desorption capabilities under different conditions, e.g., at different pHs and at different temperatures, etc. Because of this, the organic amine desulfurization solution temperature can be used to absorb sulfur dioxide at a high pH and at a low temperature and then desorb the sulfur dioxide in the desulfurization solution at a low pH and a high temperature to manufacture sulfuric acid or the like, thereby achieving removing and recycling sulfur dioxide in the flue gas.

In particular, an organic amine generally refers to an organic substance as a result of a chemical reaction between an organic-based substance and an ammonia, which is typically classified as seven kinds including aliphatic amines, alcohol amines, amides, alicyclic amines, aromatic amines, naphthalene-based amines and other types of amines. The organic amine-based compounds commonly known in the art include methylamine, ethylamine, n-propylamine, tert-butylamino ethanol (TBE), tert-butylamino-ethoxy ethanol (TBEE), 2-piperidine ethanol (PE), 2-amino-2-methyl-1-propanol (AMP), monoethanolamine (MEA), diethanolamine (DEA), triethanolamine, n-propanolamine, diisopropanolamine (DIPA), dimethyl formamide (DMF), N-methyl ethanolamine (MMEA), N-methyldiethanolamine (MDEA), (hydroxyethyl)ethylene diamine (AEE), N-tert-butylamino monoethanolamine (TBMEA), N-n-butylamino monoethanolamine (BMEA), TETA (triethylenetetramine), DETA (diethylenetriamine), sulfolane (SF), 4-(2-hydroxyethyl)-2-piperazinones, hydroxyethyl piperazine, dimethyl sulfoxide (DMSO), thiourea, dimethyl thiourea, 1,4-butanedithiol, thiodiglycol, or the like.

However, in terms of a desulfurization solution containing desulfurization organic components used in the flue gas desulfurization system, loss and consumption of the desulfurization solution is one of the problems needed to be mainly addressed in order to achieve smooth operation of the desulfurization system and reduce operation and production costs. This is because a variety of aqueous solutions including condensate water and precipitation water from an absorber, resin-washing water, condensate water from a desorber, and the like will be generated in the flue gas desulfurization system during key processes and sites such as absorbing, desorbing, resin-desalting processes, etc., and because a conversion between a sulfur-lean desulfurization solution and a sulfur-rich desulfurization solution in the desulfurization system occurs after absorbing and desorbing sulfur dioxide. Therefore, concentrations of desulfurization organic components contained in these solutions are required to be detected and analyzed in time, in order to provide detecting technical support and test data basis for process regulation such as controlling, determining and preventing causes and paths of losing desulfurization solution, deciding whether to discharge or recycle these aqueous solutions from or into a desulfurization recycling system, determining the time to add fresh desulfurization solution and the amount thereof, and so on.

At present, a to-be-measured solution in the prior art is pre-treated first by enrichment and separation technology, e.g., distillation, extraction, etc. to separate and eliminate severe interferences on measuring caused by coexistence of inorganic anions such as sulfate radical, sulfite radical, carbonate radical, chloride radical, nitrate radical, or the like, and metal cations including iron, copper, nickel, chromium, calcium, magnesium, sodium or the like, and concentrations of organic components contained in the solution is then measured by using organic analytical techniques including infrared spectroscopy, gas or liquid chromatography, gas or liquid chromatography-mass spectrometry, and nuclear magnetic resonance spectroscopy or the like. The basic principle thereof is mainly to identify and quantitatively calculate concentrations of organic amine components in the desulfurization solution by directly measuring molecular weights, molecular structures or functional groups of respective organic components existing in the solution. Such analytical methods have disadvantages, for example, complex operations, large consumption of detection equipment materials such as a chromatography column, long inspection process which usually takes 6 to 12 hours to analyze one sample and thus is difficult to satisfy requirements of real-time monitoring operational status of the desulfurization system. In addition, as for the existing gas chromatography-mass spectrometry (GC-MS) analysis method, it may cause a severe damage to an expensive capillary column during testing due to moisture, may take a long time to pre-treat a sample in distilling and separating, and may have frequent maintenance, high cost, and higher test cycle and analytical cost for equipments including an ion source, the capillary column, an injection system, a bar quadrupole mass spectrometer, and the like.

SUMMARY OF THE INVENTION

An object of the present disclosure is to address one or more problems existing in the prior art described as above.

For example, one of objects of the present disclosure is to provide a method capable of quickly determining whether desulfurization organic components exist in a relevant aqueous solution in a flue gas desulfurization process and paths and amount of loss of the desulfurization organic components, so as to provide accurate basis for finding and blocking the paths of loss of expensive organic amine components, and also capable of reducing the loss and consumption of a desulfurization solution so as to ensure stably and efficiently operate the flue gas desulfurization system and reduce operating cost.

An aspect of the present disclosure provides a method for detecting paths and amount of loss of desulfurization organic components in a flue gas desulfurization system, comprising: preparing a solution at a various process stage of the flue gas desulfurization system as a to-be-measured solution, and a pure desulfurization solution to be added to the flue gas desulfurization system for absorbing and desorbing sulfur oxides as a base standard solution, and diluting the base standard solution with water to a plurality of standard solutions containing different concentrations of desulfurization organic components; adjusting the to-be-measured solution and the plurality of standard solutions to have a strong acidity, respectively, such that each of desulfurization organic components in the to-be-measured solution and the plurality of standard solutions exists in ion forms; heating and oscillating the to-be-measured solution and the plurality of standard solutions, respectively, to substantially remove carbonate and bicarbonate ions in the to-be-measured solution; respectively detecting carbon elements in the plurality of standard solutions, to form a linear relationship between concentrations of the desulfurization organic components in the standard solutions and detected carbon element data; and detecting carbon elements in the to-be-measured solution, and obtaining a total concentration of the desulfurization organic components in the to-be-measured solution according to the linear relationship.

Another aspect of the present disclosure provides a regenerable flue gas desulfurization process. The regenerable flue gas desulfurization process comprises absorbing sulfur oxides in a flue gas at a relatively low temperature and desorbing gases of the sulfur oxides at a relatively high temperature by using a solution containing desulfurization organic components, and repeating the absorbing and the desorbing, and the process further comprises monitoring losses of the desulfurization organic components in real time by using the method for detecting paths and amount of losses of desulfurization organic components in the flue gas desulfurization system described as above.

Compared with the prior art, the present disclosure can achieve beneficial effects as follows.

First, a method of quickly detecting and determining paths, amount and reasons of loss of desulfurization organic components in a flue gas desulfurization system is provided, which can quickly monitor, analyze and efficiently control concentration of desulfurization organic components in various solutions in time, so as to provide technical support and basis test data for blocking the paths of loss of expensive desulfurization organic amine components, for recovering the desulfurization organic amine components, and determining the time for complementing fresh desulfurization solution and an amount thereof to maintain stable operation of the system, and thus can achieve reduction of the loss and consumption of the desulfurization solution, can ensure stably and efficiently operate the flue gas desulfurization system, and can reduce operating cost.

Second, total concentrations of desulfurization organic components in respective solutions are indirectly calculated by measuring signal intensities or contents of carbon elements contained in desulfurization solutions at respective process stages such as absorbing, desorbing, desalting, washing, etc. in an organic amine flue gas desulfurization system through an inorganic element detecting means, thereby capable of quickly deciding the paths and amount of the desulfurization organic components in the desulfurization system. In addition, the method according to the present disclosure avoids complex pre-treatment steps including distillation or extraction separation, is less influenced by measuring interference or human factors, greatly simplifies medium processes, can be operated simply and easily, and has very short test period, which takes no more than 15 minutes for the entire operation. Meanwhile, the method according to the preset disclosure is suitable for simultaneously analyzing a large numbers of samples, is better than traditional methods such as GC-MS requiring 6~12 hours, and has a very low analysis and test cost, as well as avoiding incomplete oxidation of organic amine-based desulfurization components, evaporation loss upon evaporating concentrated moisture or other technical difficulties caused by the current total organic carbon measuring method through oxidation of organic compounds.

BRIEF DESCRIPTION OF THE DRAWINGS

FIG. 1 illustrates a calibration graph of a total concentration of a pure desulfurization organic amine component standard solution according to an exemplary embodiment of the present disclosure.

DETAILED DESCRIPTION OF THE PREFERRED EMBODIMENTS

Hereinafter, embodiments of the present disclosure will be described in detail in conjunction with the attached drawing.

According to one aspect of the present invention, a method for detecting paths and amount of loss of desulfurization organic components in a flue gas desulfurization system comprises steps of: preparing a solution at a various process stage of the flue gas desulfurization system as a to-be-measured solution, and a pure desulfurization solution to be added to the flue gas desulfurization system for absorbing and desorbing sulfur oxides as a base standard solution (hereinafter, also referred to as a pure desulfurization organic amine component standard solution), and diluting the base standard solution with water to a plurality of standard solutions containing different concentrations of desulfurization organic components; adjusting the to-be-measured solution and the plurality of standard solutions to have a strong acidity, respectively, such that each of desulfurization organic components in the to-be-measured solution and the plurality of standard solutions exists in an ion form, which can avoid the organic desulfurization components from being evaporated due to heat during a subsequent heating process; heating and oscillating the to-be-measured solution and the plurality of standard solutions, respectively, to substantially remove carbonate and bicarbonate ions in the to-be-measured solution, so as to achieve a purpose of separating and eliminating inorganic carbides in the desulfurization solution while remaining organic amine desulfurization components to be measured, thereby preventing inorganic carbon elements from interfering with measuring on organic carbon elements; respectively detecting carbon elements in the plurality of standard solutions, to form a linear relationship between concentrations of the desulfurization organic components in the standard solutions and detected carbon element data (e.g., the detected carbon element data can be related to intensities or contents of the carbon elements); and detecting carbon elements in the to-be-measured solution, and obtaining a total concentration of the desulfurization organic components in the to-be-measured solution according to the linear relationship.

In an exemplary embodiment of the method of the present disclosure, the solution at a various process stage of the flue gas desulfurization system includes various aqueous solutions such as condensate water and precipitation water from an absorber, resin-washing water, condensate water from a desorber, a sulfur-lean desulfurization solution and a sulfur-rich desulfurization solution, etc. In general, in the method of the present disclosure, the desulfurization solution as the to-be-measured solution is a solution containing desulfurization organic components capable of absorbing sulfur oxides including sulfur dioxide and sulfur trioxide in the flue gas at a lower temperature and desorbing the sulfur oxides at a higher temperature, and for example, the to-be-measured solution of the present disclosure can be an organic amine desulfurization solution. Specifically, with regard to the organic amine desulfurization solution as the to-be-measured solution of the present disclosure, it can be an originally mixed solution (i.e., "new desulfurization solution", which can also be used as a base standard solution) prepared from one or more organic amine-based compounds and water as well as other antioxidant and the like for repeatedly absorbing and desorbing sulfur dioxide in various industrial flue gas such as in metallurgical sintering flue gas; can be a desulfurization solution formed by the originally mixed solution having absorbed sulfur dioxide in the industrial flue gas, i.e., the sulfur-rich desulfurization solution; can be a desulfurization solution regenerated by the sulfur-rich desulfurization solution having desorbed and released the sulfur dioxide absorbed therein, i.e., the sulfur-lean desulfurization solution; or can be various aqueous solutions generated at several key processes and sites such as absorbing, desorbing and resin-desalting processes of the flue gas desulfurization system via an organic amine method, which generally refers to condensate water or precipitation water generated in the absorber for absorbing sulfur dioxide, washing water generated at a desalting process using an ion exchange resin, condensate water desorbed in the desorber from the desulfurization solution having absorbed sulfur dioxide, or the like. In view of the organic amine desulfurization solution being one typical example of the desulfurization solution containing organic components for desulfurizing, the method of the present disclosure will be hereinafter explained by taking the organic amine desulfurization solution as an example; however, the desulfurization solution detected by the method of the present disclosure is not limited thereto.

In a preferable exemplary embodiment of the method of the present disclosure, the adjusting of the to-be-measured solution and the plurality of standard solutions comprises adjusting pH values of the to-be-measured solution and the plurality of standard solutions to be in a range of 1~2, respectively, and thus all the desulfurization organic components in the to-be-measured solution and the plurality of standard solutions can be ensured to exist in ion forms. For example, the adjusting of the to-be-measured solution and the plurality of standard solutions may be achieved by adding a sulfuric acid solution or a nitric acid solution to the to-be-measured solution and the plurality of standard solutions, respectively, and in this case, the sulfuric acid solution can be prepared by mixing a strong sulfuric acid having a concentration of 95~98% by mass and water in a volume ratio of (2~4):1, e.g., a volume ratio of 3:1.

The to-be-measured solution is adjusted to have a strong acidity, e.g., a pH of 1~2, by using the above sulfuric acid solution, of which the main purpose is to ensure that, under a condition of hydrogen ion having a significantly excessive amount, organic amine components in a weak basic state possibly present in the solution sufficiently combine with hydrogen ions to generate organic amine cations, and thus can be prevented from being in molecular forms, thereby greatly reducing volatility of the desulfurization organic amine components and enhancing stability thereof. This can avoid volatilization of the desulfurization organic amine components from interfering with precision of a measurement. Meanwhile, the sulfuric acid newly introduced into the to-be-measured solution does not affect the measuring result due to sulfate ions ($SO_4^{2-}$) or sulfite ions ($SO_3^{2-}$) originally existing in the to-be-measured solution. Also, a sulfuric acid commercially available has a concentration much greater than that of a hydrochloric acid, a nitric acid or the like. Since a sulfuric acid molecule contains two hydrogen ions, the sulfuric acid can be used in an amount much less than other acids in terms of adjusting an acidity of a desulfurization solution. As a result, the sulfuric acid added substantially does not affect a change of a total volume of the desulfurization solution; that is to say, upon adding the sulfuric acid to adjust the acidity of the desulfurization solution, the total volume of the desulfurization solution is not substantially changed because of a usage of the sulfuric acid being very little, causing no substantial change to the total volume of the desulfurization solution, and the solution is not thus diluted. Therefore, in the present disclosure, an appropriate amount of the desulfurization solution is weighed, is adjusted to have a controllable acidity, and decomposes to remove carbonates therein, without any operation such as evaporating/concentrating, diluting/fixing a volume, or the like, thereby simplifying intermediate steps and shortening analyzing process, as well as avoiding a relative concentration of the organic amine components to be measured from being reduced due to evaporation or loss and ensuring the precision of the measurement. Similarly, the citric acid solution can also be used to adjust the acidity of the desulfurization solution to be measured to be strong, since nitric ions are generally contained in the desulfurization solution to be measured.

In a preferable exemplary embodiment of the method of the present disclosure, the heating and oscillating the to-be-measured solution and the plurality of standard solutions, respectively, comprises heating the to-be-measured solution and the plurality of standard solutions to a temperature of 75~95° C. For example, the heating can be performed by means of a water bath. Inorganic carbon elements (generally in forms of carbonate and bicarbonate radicals) possibly present in the to-be-measured solution and the plurality of standard solutions combine with hydrogen ions in a short time in a temperature range of 75~95° C., and then are discharged in a form of carbon dioxide gas, and thus can be removed more quickly.

In a preferable exemplary embodiment of the method of the present disclosure, the respectively detecting of the carbon elements in the plurality of standard solutions and the detecting of the carbon element in the to-be-measured solution are performed by using an inductively coupled plasma-mass spectrometric method or an inductively coupled plasma-atomic emission spectroscopic method. However, the present disclosure is not limited thereto, and to those skilled in the art, they can adopt other methods to detect the carbon elements in the to-be-measured solution and the plurality of standard solutions. In addition, in a case of performing detection by using the inductively coupled plasma-mass spectrometric method or the inductively coupled plasma-atomic emission spectroscopic method, the respectively detecting of the carbon elements in the plurality of standard solutions comprises controlling contents of the desulfurization organic components in the plurality of standard solutions preferably to be in a range of 0 g/L~30 g/L, and the detecting of the carbon element in the to-be-measured solution comprises controlling a total content of the desulfurization organic components in the to-be-measured solution preferably to be in a range of 0.05 g/L~30 g/L, thereby making operations more convenient and quick, and capable of further improving the precision of the measurement. However, the total content of the desulfurization organic components in the to-be-measured solution detected in the method of the present disclosure is not limited thereto; that is to say, the total content of the desulfurization organic components in the to-be-measured solution detected in the method of the present disclosure can be higher than 30 g/L or lower than 0.05 g/L. For instance, in a case of a sample of a to-be-measured desulfurization solution having a higher concentration of desulfurization organic components such as a sulfur-lean desulfurization solution, a sulfur-rich desulfurization solution or the like, it may be firstly diluted with water (a diluting ratio may be 5~50 times), and then may be detected for the carbon element, after pre-treatments including adjusting an acidity by using the sulfuric acid and oscillating in a hot water bath, etc.

According to another aspect of the present disclosure, a regenerable flue gas desulfurization process comprises absorbing sulfur oxides in a flue gas at a relatively low temperature and desorbing gases of the sulfur oxides at a relatively high temperature by using a solution containing desulfurization organic components, and repeating the absorbing and the desorbing, and further comprises monitoring losses of the desulfurization organic components in real time by using the method for detecting paths and amount of losses of desulfurization organic components in the flue gas desulfurization system described as above.

In summary, the method for detecting paths and amount of loss of desulfurization organic components in a flue gas desulfurization system according to the present disclosure has advantages as follow.

Firstly, a total concentration of desulfurization organic components in a solution is not directly measured by using a method or technique of analyzing organic compounds, but quickly and indirectly detected measured by a technique of analyzing inorganic elements, so that a total concentration of the organic amine components can be indirectly calculated so as to determine whether desulfurization organic components are present or not in the solution. The technical point of the method is completely different from that in a traditional method by detecting organic substances, and thus makes the operation convenient and quick, interference factors less, and a period for measuring no more than 15 minutes.

Secondly, with regard to the method of directly measuring a content of carbon by using the inductively coupled plasma-mass spectrometric method, the inductively coupled plasma-atomic emission spectroscopic method, or the like, the basic principle thereof is that organic substances in the sample are dissociated or ionized to single carbon ions through a torch of an inductively coupled plasma (ICP) up to approximately 10000K (i.e., a high temperature), and are then separated from other co-existing elements based on a ratio of a total mass to the number of charges of the carbon ions (i.e., a mass-to-charge ratio) in a mass analyzer, and a signal intensity or content of the carbon elements is finally measured, so that a total amount of concentration of the desulfurization organic components can be thus calculated.

Thirdly, in the method of the present disclosure, the to-be-measured solution is less influenced by the co-existing components therein and human factors, and inorganic anions such as a nitrate radical, a fluorine ion, a carbonate radical, a sulfate radical, a sulfite radical, a chloride ion, and/or the like, and metal cations such as nickel, chromium, calcium, magnesium, potassium, sodium, iron, copper, lead, aluminum and/or the like, which co-exist in a complex matrix of the desulfurization solution, have no interference on the measuring result, thereby obtaining high accuracy and precision. The method has less requirements on an operator, has little contamination or effect on a testing instrument, has a low analytical cost, and is capable of simultaneously measuring a large number of samples, and thus can provide timely detecting data for regulating process parameters and reducing loss and consumption of the desulfurization solution.

In conclusion, the method of the present disclosure described as above is completely different from the prior technical means or methods of detecting organic substances and the prior interfering external factors and method of eliminating the same. The solution used is to directly detect organic carbon elements in a sample solution by means of an ICP-MS, an ICP-OES, or the like, so that a total concentration amount of organic amine components contained in the solution can be indirectly calculated. As compared to existing organic analytical methods by using a chromatography or mass spectrometry, the method in the present disclosure has relatively less operational processes, is more convenient and quick, greatly shortens analysis process, and reduces detecting period from 6~12 hours to no more than 15 minutes, and factors including the co-existing complex matrix components, human operations and so on has less influence on measurement. Meanwhile, the method in the present disclosure has an improved anti-jamming capability, has an increased accuracy and precision level, consumes less expensive chromatography column unlike in the prior method, and has a considerably low analytical cost. However, with respect to organic chromatographic analysis method capable of measuring concentration components of respective desulfurization organic amine components in a desulfurization solution such as GC, GC-MS, LC, LC-MS, etc., the method according to the present disclosure is used to measure a sum of concentrations of respectively desulfurization organic amine components in a desulfurization solution, that is, a total concentration of the desulfurization organic amine components, and cannot be used to respective concentration (i.e., concentration components) of respective organic amine components in the desulfurization solution.

In another specific exemplary embodiment of the present disclosure, the method according to the present disclosure decomposes inorganic carbonates in various desulfurization solutions by adjusting pH values thereof with a sulfuric acid solution to eliminate interference caused by inorganic carbon elements on the measurement of organic carbon elements, and directly measures signal intensity or content of the organic carbon elements in the desulfurization solution by using an inorganic element detecting means such as ICP-MS, ICP-OES, etc., and thus indirectly calculates a total concentration of the desulfurization organic components contained in the desulfurization solution, wherein the sulfuric acid solution is obtained by mixing an analytical pure strong sulfuric acid having a concentration of 95~98% by mass and water in a volume ratio of 3:1, which can also be referred to as (3+1) sulfuric acid. Here, the ICP-MS means can be ELAN 9000-type available from P-E Co., U.S., and a HY-5-type cyclotron oscillator can be used in an exemplary embodiment of the present disclosure.

Specific detecting and analyzing operations in the example embodiments are described as follows: each of various desulfurization solutions is taken in a volume of 100 mL~200 mL into an Erlenmeyer flask, then adjusted to have a pH value of 1~2 by dropping a suitable amount of (3+1) sulfuric acid therein, placed in a hot water bath with a temperature of 75° C.~95° C., and then oscillated by a cyclotron oscillator for 5~10 mins. By using an inorganic element detecting means such as ICP-MS, ICP-OES or the like, signal intensities of carbon ions ionized or carbon spectrums of carbon elements excited (in particular, signal intensities of mass spectrums of carbon ions in examples as below) were directly measured, and a standard curve of concentrations of pure desulfurization organic amine component standard solutions was thus drawn, thereby calculating a total concentration of organic components in various desulfurization solutions. Specific parameters and resulting data are given in examples shown as below.

Example 1

Detection and Analysis of a Total Concentration of Organic Desulfurization Components in a Precipitation Water from an Absorber The precipitation water from the absorber (hereinafter referred to as "Sample 1#") was taken in a volume of 100 mL into an Erlenmeyer flask, adjusted to have a pH value of 1.0 by adding a suitable amount of (3+1) sulfuric acid therein, placed in a hot water bath with a temperature of 75° C., and then oscillated by the cyclotron oscillator for 5 mins.

A signal intensity of mass spectrum generated by carbon ions ionized by organic carbon elements in the solution was directly measured by means of an ICP-MS, for drawing a standard curve based on pure desulfurization organic amine component standard solutions, and a total concentration of organic components contained in the precipitation water was calculated. Measuring operation through the ICP-MS were taken in a general manner, in which operation parameters used in an inductively coupled plasma mass spectrometer were listed as following: an ICP power being 1250 W; a flow rate being a cooling air of 12 L/min; a flow rate of an auxiliary gas being 0.85 L/min; a flow rate of an atomizing air being 0.92 L/min; a feed rate being 0.90 mL/min; a standard resolution being 0.7 amu; a dwell time being 100 ms; a pulse detector (PC Detector) having an operation voltage of 2650 v; and an analog detector (Analogue Detector) having an operation voltage of 1550 v.

Example 2

Detection and Analysis of a Total Concentration of Organic Desulfurization Components in a Condensate Water from the Absorber The condensate water from the absorber (hereinafter referred to as "Sample 2#") was taken in a volume of 200 mL, adjusted to have a pH value of 2.0, placed in a hot water bath with a temperature of 95° C., and then oscillated for 10 mins. Except for the above, a total concentration of organic components contained in the condensate water was measured by using the ICP-MS and calculated according the same method as in Example 1.

Example 3

Detection and Analysis of a Total Concentration of Organic Desulfurization Components in a Washing Water The washing water (hereinafter referred to as "Sample 3#") was taken in a volume of 150 mL, adjusted to have a pH value of 1.5, placed in a hot water bath with a temperature of 80° C., and then oscillated for 8 mins. Except for the above, a total concentration of organic components contained in the washing water was measured by using the ICP-MS and calculated according the same method as in Example 1.

Example 4

Detection and Analysis of a Total Concentration of Organic Desulfurization Components in a Condensate Water from a Desorber The condensate water from the desorber (hereinafter referred to as "Sample 4#") was taken in a volume of 120 mL, adjusted to have a pH value of 1.0, placed in a hot water bath with a temperature of 85° C., and then oscillated for 6 mins. Except for the above, a total concentration of organic components contained in the condensate water was measured by using the ICP-MS and calculated according the same method as in Example 1.

Example 5

Detection and Analysis of a Total Concentration of Organic Desulfurization Components in a Sulfur-Lean Desulfurization Solution The sulfur-lean desulfurization solution (hereinafter referred to as "Sample 5#") was taken in a volume of 150 mL, adjusted to have a pH value of 1.5, placed in a hot water bath with a temperature of 90° C., and then oscillated for 7 mins, followed by being diluted to have a concentration of one fifth of its original concentration. Except for the above, a total concentration of organic components contained in the condensate water was measured by using the ICP-MS and calculated according the same method as in Example 1.

Example 6

Detection and Analysis of a Total Concentration of Organic Desulfurization Components in a Sulfur-Lean Desulfurization Solution The sulfur-lean desulfurization solution (hereinafter referred to as "Sample 6#") was taken in a volume of 150 mL, adjusted to have a pH value of 2.0, placed in a hot water bath with a temperature of 95° C., and then oscillated for 10 mins, followed by being diluted to have a concentration of one fiftieth of its original concentration. Except for the above, a total concentration of organic components contained in the condensate water was measured by using the ICP-MS and calculated according the same method as in Example 1.

Example 7

Detection and Analysis of a Total Concentration of Organic Desulfurization Components in a Sulfur-Rich Desulfurization Solution The sulfur-rich desulfurization solution (hereinafter referred to as "Sample 7#") was taken in a volume of 200 mL, adjusted to have a pH value of 1.0, placed in a hot water bath with a temperature of 95° C., and then oscillated for 10 mins, followed by being diluted to have a concentration of one tenth of its original concentration. Except for the above, a total concentration of organic components contained in the condensate water was measured by using the ICP-MS and calculated according the same method as in Example 1.

Example 8

Detection and Analysis of a Total Concentration of Organic Desulfurization Components in a Sulfur-Rich Desulfurization Solution The sulfur-rich desulfurization solution (hereinafter referred to as "Sample 8#") was taken in a volume of 200 mL, adjusted to have a pH value of 1.0, placed in a hot water bath with a temperature of 95° C., and then oscillated by the cyclotron oscillator for 10 mins, followed by being diluted to have a concentration of one twenty-fifth of its original concentration. Except for the above, a total concentration of organic components contained in the condensate water was measured by using the ICP-MS and calculated according the same method as in Example 1.

Example 9

Detection and Analysis of a Total Concentration of Organic Desulfurization Components in a Washing Water The washing water (hereinafter referred to as "Sample 9#") was taken in a volume of 180 mL, adjusted to have a pH value of 1.0, placed in a hot water bath with a temperature of 95° C., and then oscillated by the cyclotron oscillator for 9 mins. Except for the above, a total concentration of organic components contained in the condensate water was measured by using the ICP-MS and calculated according the same method as in Example 1.

Example 10

Drawing of a Standard Curve Based on Concentrations of Pure Desulfurization Organic Amine Component Standard Solutions A series of standard solutions were prepared with a total concentration of pure desulfurization organic amine components of 0.00 g/L, 0.05 g/L, 0.10 g/L, 0.30 g/L, 0.50 g/L, 1.00 g/L, 3.00 g/L, 5.00 g/L, 10.0 g/L, 20.0 g/L, and 30.0 g/L, respectively, and standard solutions obtained thereby were taken in respective volumes of 100 mL, adjusted to have a pH value of 1.0, placed in a hot water bath with a temperature of 95° C., and then oscillated for 10 mins. Except for the above, respective total concentrations of organic components contained in the washing water were measured by using the ICP-MS as in Example 1.

A standard curve was obtained by taking signal intensities of measured organic carbon elements as a horizontal axis and respective total concentrations of pure desulfurization organic amine component standard solutions as a vertical axis, as shown in FIG. 1. It shows that the standard curve obtained as above had a good linear relationship, which had a relevant coefficient greater than 0.999, and thus ensured accuracy of testing results.

Example 11

Precision Test

Samples 1#, 3#, 5# and 7# were repeatedly pre-treated and measured for eight times, respectively, according to Examples 1, 3, 5 and 7, and measurement results of eight times were used to estimate precision of the method according to the present disclosure based on an relative standard deviation (RSD). The results are shown in Table 1.

TABLE 1

| Precision text (n = 8) Total concentration of desulfurization organic components | | | |
|---|---|---|---|
| Sample 1# | | Sample 3# | |
| Measurement mean (g/L) | Relative standard deviation (%) | Measurement mean (g/L) | Relative standard deviation (%) |
| 0.63 | 2.85 | 3.27 | 2.04 |
| Sample 5# | | Sample 7# | |
| Measurement mean (g/L) | Relative standard deviation (%) | Measurement mean (g/L) | Relative standard deviation (%) |
| 114.9 | 0.75 | 69.03 | 1.39 |

It can be seen from Table 1 that the RSD in the present disclosure can be less than 3%, showing relatively high precision, good stability and excellent operability.

Example 12

Recovery Test

TABLE 12

| Recovery test | | | | |
|---|---|---|---|---|
| Total concentration of desulfurization organic components (g/L) | | | | |
| Sample Nos. | Measurement value before standard addition | Amount of standard addition | Measurement value after standard addition | Recovery (%) |
| 2# | 0.8713 | 1.000 | 1.857 | 98.57 |
| 4# | 1.779 | 1.000 | 2.831 | 105.20 |
| 6# | 59.22 | 20.00 | 80.05 | 104.20 |
| 8# | 68.55 | 20.00 | 88.03 | 97.40 |

Samples 2#, 4#, 6# and 8# were recovered through standard addition, respectively, and it can be known from Table 2 that the present disclosure can have a recovery in a range of 97.40%~105.20%, showing relatively high accurate and reliable results of analysis.

Although the present disclosure has been described in connection with the accompanying drawings and exemplary embodiments as above, it should be apparent to one of ordinary skill in the art that the above embodiments can be variously modified without departing from the spirit and scope of the claims.

What is claimed is:

1. A method for detecting paths and amount of loss of desulfurization organic components in a flue gas desulfurization system, comprising:
    preparing a solution at a various process stage of the flue gas desulfurization system as a to-be-measured solution, and a pure desulfurization solution to be added to the flue gas desulfurization system for absorbing and desorbing sulfur oxides as a base standard solution, and diluting the base standard solution with water to a plurality of standard solutions containing different concentrations of desulfurization organic components;
    adjusting the to-be-measured solution and the plurality of standard solutions to have a strong acidity, respectively, such that each of desulfurization organic components in the to-be-measured solution and the plurality of standard solutions exists in ion forms;
    heating and oscillating the to-be-measured solution and the plurality of standard solutions, respectively, to substantially remove carbonate and bicarbonate ions in the to-be-measured solution;
    respectively detecting carbon elements in the plurality of standard solutions, to form a linear relationship between concentrations of the desulfurization organic components in the standard solutions and detected carbon element data; and
    detecting carbon elements in the to-be-measured solution, and obtaining a total concentration of the desulfurization organic components in the to-be-measured solution according to the linear relationship.

2. The method of claim 1, wherein the solution at a various process stage of the flue gas desulfurization system includes condensate water from an absorber, precipitation water from an absorber, resin-washing water, condensate water from a desorber, a sulfur-lean desulfurization solution or a sulfur-rich desulfurization solution.

3. The method of claim 1, wherein the adjusting of the to-be-measured solution and the plurality of standard solutions comprises adjusting pH values of the to-be-measured solution and the plurality of standard solutions to be in a range of 1~2, respectively.

4. The method of claim 1, wherein the adjusting of the to-be-measured solution and the plurality of standard solutions comprises adding a sulfuric acid solution or a nitric acid solution to the to-be-measured solution and the plurality of standard solutions, respectively, and wherein the sulfuric acid solution is obtained by mixing a strong sulfuric acid having a concentration of 95~98% by mass and water in a volume ratio of (2~4):1.

5. The method of claim 1, wherein the heating and oscillating the to-be-measured solution and the plurality of standard solutions, respectively, comprises heating the to-be-measured solution and the plurality of standard solutions to a temperature of 75~95° C.

6. The method of claim 1, wherein the respectively detecting of the carbon elements in the plurality of standard solutions and the detecting of the carbon element in the to-be-measured solution can be performed by using an inductively coupled plasma-mass spectrometric method or an inductively coupled plasma-atomic emission spectroscopic method.

7. The method of claim 6, wherein the respectively detecting of the carbon elements in the plurality of standard solutions comprises controlling contents of the desulfurization organic components in the plurality of standard solutions to be in a range of 0 g/L~30 g/L, and the detecting of the carbon elements in the to-be-measured solution comprises controlling a total content of the desulfurization organic components in the to-be-measured solution to be in a range of 0.05 g/L~30 g/L.

8. A regenerable flue gas desulfurization process, comprising absorbing sulfur oxides in a flue gas at a relatively low temperature and desorbing gases of the sulfur oxides at a relatively higher temperature by using a solution containing desulfurization organic components, and repeating the absorbing and the desorbing, wherein the process further comprises monitoring losses of the desulfurization organic components in real time by using the method for detecting paths and amount of losses of desulfurization organic components in the flue gas desulfurization system according to claim 1.

* * * * *